United States Patent [19]

Razumov et al.

[11] 4,162,264
[45] Jul. 24, 1979

[54] PROCESS FOR PREPARING DIPHENYLPHOSPHINYLACETIC ACID HYDRAZIDE

[76] Inventors: Alexandr I. Razumov, ulitsa Akademika Gubkina, 17, kv. 34; Raisa I. Tarasova, ulitsa 8 Marta, 2, kv. 28; Valentina G. Nikolaeva, ulitsa Kurchatova, 4, kv. 66; Rimma L. Yafarova, ulitsa Zhdanova, 66, kv. 62, all of Kazan, U.S.S.R.

[21] Appl. No.: 839,554

[22] Filed: Oct. 5, 1977

[51] Int. Cl.$^2$ ............................................ C07C 102/00
[52] U.S. Cl. .................................................. 260/558 H
[58] Field of Search .................................... 260/558 H

[56] References Cited
U.S. PATENT DOCUMENTS

| | | | |
|---|---|---|---|
| 2,899,424 | 8/1959 | Rudner | 260/558 H X |
| 2,953,570 | 9/1960 | Rudner | 260/558 H X |
| 3,485,806 | 12/1969 | Bloomquist et al. | 260/558 H X |
| 3,946,131 | 3/1976 | Biefeld et al. | 260/558 H X |

*Primary Examiner*—Thomas Waltz
*Attorney, Agent, or Firm*—Lackenbach, Lilling & Siegel

[57] ABSTRACT

The process according to the present invention comprises reacting diphenylchlorophosphine with ethylene oxide in a medium of an inert organic solvent. The resulting reaction mixture is heated in the presence of an alkyl ester of a haloacetic acid until the formation of an alkyl ester of diphenylphosphinylacetic acid. The latter, without separation and any additional purification, is reacted with hydrazine hydrate. The advantage of the process according to the present invention resides in a simplified technology, preparation of the desired product in a single stage at a high yield and the use of readily available commercially produced reagents.

7 Claims, No Drawings

PROCESS FOR PREPARING DIPHENYLPHOSPHINYLACETIC ACID HYDRAZIDE

FIELD OF THE INVENTION

The present invention relates to the production of organophosphorous compounds and, more specifically, to processes for preparing diphenylphosphinylacetic acid hydrazide of the formula:

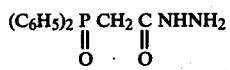

This compound reveals biologically active properties, wherefore it is of a great commercial importance. This compound can serve as a starting product for the production of other compounds also featuring biological activity.

BACKGROUND OF THE INVENTION

Known in the art is a process for preparing diphenylphosphinylacetic acid hydrazide (DPAH) which comprises interaction of diphenylchlorophosphine with ethanol in the medium of ethyl ether in the presence of triethylamine; separation, by filtration, of the resulting triethylamine hydrochloride; distilling-off the solvent and separation of ethyl ester of diphenylphosphinic acid by distillation. The thus-prepared ethyl ester of diphenylphosphinous acid is converted to ethyl ester of diphenylphophinylacetic acid by reaction with ethyl ester of chloroacetic acid at a temperature within the range of from 100° to 140° C. Then the resulting ethyl ester of diphenylphosphinylacetic acid is dissolved in benzene and recovered from hexane to purify it from the by-products of the reaction. The purified ethyl ester of diphenylphosphinylacetic acid is reacted with hydrazine hydrate at a temperature within the range of from 140° to 150° C., followed by isolation of the desired product and recrystallization thereof from ethanol (cf. Journal of General Chemistry).

The prior art process is a multi-stage process performed under severe temperature conditions and contemplating the use of auxiliary components in certain intermediate reactions as well as hazardous solvents. To ensure the required quality of the desired product in the first stage of the process, it is necessary to purify ethyl ester of diphenylphosphinous acid.

All the above-mentioned features substantially complicate the process and make it difficult to be commercially implemented.

OBJECTS AND SUMMARY OF THE INVENTION

It is an object of the present invention to provide a simplified technology for the preparation of diphenylphosphinylacetic acid hydrazide which would be suitable for commercial implementation.

It is another object of the present invention to provide a single-state process for the preparation of the above-mentioned desired product.

Still another object of the present invention is to provide a process for the preparation of the above-mentioned product which would enable a reduced duration of the production cycle.

These objects are accomplished by a process for the preparation of diphenylphosphinylacetic acid hydrazide which according to the present invention involves reacting diphenylchlorophosphine with ethylene oxide in a medium of an inert organic solvent, heating of the reaction mixture in the presence of an alkyl ester of a haloacetic acid until the formation of an alkyl ester of diphenylphosphinylacetic acid, reacting the alkyl ester of diphenylphosphinylacetic acid with hydrazine hydrate.

The process according to the present invention has certain advantages residing in a simplified technology and single-stage character of the process.

In accordance with the present invention, interaction of diphenylchlorophosphine and ethylene oxide is effected in a stoichiometric ratio of the components. As an organic solvent, use may be made of methylene chloride, chloroform, benzene, hexane, petroleum ether and an alkyl ester of a haloacetic acid and other organic solvents which are inactive in this particular process. The reaction between diphenylchlorophosphine and ethylene oxide can be performed at a temperature within the range of from $-5°$ to $+30°$ C., though it is preferable to limit the upper value to $+20°$ C. since above 20° C. side reactions are possible which result in losses of ethylene oxide and substantial increase in the process duration. At the same time, a temperature below $-5°$ C. does not exert any noticeable effect upon the product yield and quality, though it necessitates substantial increase in the production costs due to the provision of a cooling system.

In accordance with the present invention, the reaction mixture obtained in the reaction between diphenylchlorophosphine and ethylene oxide should be heated to a temperature within the range of from 60° to 140° C. This temperature is optimal for the preparation of an alkyl ester of diphenylphosphinylacetic acid, though the formation of said ester can start already at a temperature below 60° C.

The reaction between said alkyl ester of diphenylphosphinylacetic acid and hydrazine hydrate should be preferably performed at a temperature within the range of from 40° to 60° C. The reaction temperature below 40° C. substantially lowers the process speed, while that above 60° C. results in troubles in the process conditions maintained by side reactions and ejections of the reactants.

The main advantage of the present invention is that it makes possible: to obtain the desired product in a single stage at high purity and at a high yield. Another advantage of the process according to the present invention is that it makes possible to reduce the number of the reagents employed, eliminate certain operations (such as filtration, separation and purification of intermediates). reduce total power consumption as well as reduce the total process duration. Still another advantage of the present invention resides in a substantial limitation of the total volume and range of solvents used in the process; the possibility of replacing hazardous solvents (ether) with less flammable ones (methylene chloride, chloroform).

In the case of using, as a solvent, an alkyl ester of a haloacetic acid, the necessity of using other solvents is avoided. The starting reagents as employed in the process according to the present invention are produced on an industrial scale and comprise commercial products.

DETAILED DISCLOSURE

The process according to the present invention is practically performed in the following manner.

Into a flask provided with a thermometer, stirrer, gas-supply pipe and a cooler there are charged diphenylchlorophosphine and an inert organic solvent such as methylene chloride. The system is purged with an inert gas and cooled to −5° C. Thereafter, ethylene oxide in a mixture with an inert gas is passed through the solution of diphenylchlorophosphine at a temperature of the reaction mixture within the range of from −5° to +20° C. On completion of the reaction with ethylene oxide, into the reaction mixture containing β-chloroethyl ester of diphenylphosphinous acid, an alkyl ester of a haloacetic acid is added. As the alkyl esters of a haloacetic acid use can be made of methyl ester of chloroacetic acid, ethyl ester of chloroacetic acid, methyl ester of bromoacetic acid, ethyl ester of bromoacetic acid and the like. The alkyl ester of a haloacetic acid can be used as an inert reaction medium in the reaction of diphenylchlorophosphine with ethylene oxide. No other solvents are needed in this case.

The reaction mixture is gradually heated to a temperature within the range of from 60° to 140° C. in the presence of the alkyl ester of the haloacetic acid. In doing so, the β-chloroethyl ester of diphenylphosphinous acid reacts with the alkyl ester of the haloacetic acid to give an alkyl ester of diphenylphosphinylacetic acid and dihaloethane. During heating said dihaloethane and the solvent are gradually distilled-off. On completion of the reaction an excessive amount of the solvent and dihaloethane is removed from the reaction mixture and the remaining alkyl ester of diphenylphosphinylacetic acid is treated with hydrazine hydrate, while maintaining the reaction mixture at a temperature within the range of from 40° to 60° C. After cooling the resulting hydrazide of diphenylphosphinylacetic acid is crystallized. The crystals of the product are filtered-off, washed and air-dried. The product is recyrstallized from an alcohol or another suitable solvent. The thus-prepared product corresponds to the formula:

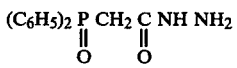

As has been mentioned hereinabove, the product reveals biologically active properties.

In experiments on animals (mice, rabbits) diphenylphosphinylacetic acid hydrazide (DPAH) reveals a central adrenolytic, N-cholinolytic and antiserotonin effects. It possesses a slight analgetic and hypothermal effects and enhances a hypothermal effect of aminazine (chloropromazine). The compound, when administered to animals, exerts no peripheral effect; neither does it causes changes in blood composition nor anatomic and histological changes in internal organs.

For a better understanding of the present invention some specific Examples illustrating the process for preparing diphenylphosphinylacetic acid hydrazide are given hereinbelow.

EXAMPLE 1

Into a 0.15 l four-neck flask provided with a thermometer, stirrer, gas-supply pipe and a cooler there are charged 33.07 g (0.15 mole) of diphenylchlorophosphine and 18.37 g (0.15 mole) of ethyl ester of chloroacetic acid. The flask contents are purged with nitrogen and cooled to the temperature of −5° C. Thereafter, a mixture of ethylene oxide and nitrogen in the ratio of 1:1 is bubbled into the solution at a temperature of the reaction mixture of from −5° to +5° C. After addition of 6.6 g (0.15 mole) of ethylene oxide and completion of the reaction, the temperature is slowly elevated to 140° C. simultaneously distilling-off dichloroethane. In doing so, ethyl ester of diphenylphosphinylacetic acid is formed.

The remaining amount of dichloroethane and unreacted ethyl ester of chloroacetic acid are removed under vacuum (residual pressure 10–15 mm Hg) at the temperature of 100° C. The reaction mixture is cooled to 40° C., added with 22.5 g (0.45 mole) of hydrazine hydrate while maintaining temperature within the range of from 40° to 60° C. After cooling, the flask contents are crystallized for 1–2 hours. The crystals are filtered-off, washed with 10 ml of an alcohol and air dried. The crystalline diphenylphosphinylacetic acid hydrazide is purified by recrystallization from ethanol. The product yield is 27 g (70% of the theoretical amount); melting point 159°–161° C. Found, %: C 61.37; 61.28; H 5.39; 5.43; N 10.25; 10.31; P 11.54; 11.62; $C_{14}H_{15}N_2O_2P$. Calculated, %: C 61.31; H 5.47; N 10.20; P 11.31.

EXAMPLE 2

The process is performed as in the foregoing Example 1, except that the reaction of diphenylchlorophosphine with ethylene oxide is conducted at the temperature of 20° C.

EXAMPLE 3

The process is performed in a manner similar to that described in the foregoing Example 1, except that the reaction of diphenylchlorophosphine with ethylene oxide is conducted in the medium of methylene chloride. On completion of the reaction with ethylene oxide, the reaction mixture is added with 18.37 g (0.15 mole) of chloroacetic acid ethylate. The reaction mixture is heated as described in Example 1 hereinbefore simultaneously distilling-off dichloroethane and methylene chloride. Further operations of the process are conducted following the procedure described in the foregoing Example 1.

EXAMPLE 4

The process is performed following the procedure of the foregoing Example 1, except that the reaction between diphenylchlorophosphine and ethylene oxide is conducted in the medium of methyl ester of chloroacetic acid.

EXAMPLE 5

The process is performed in a manner similar to that described in Example 1 hereinbefore, except that the reaction between diphenylchlorophosphine and ethylene oxide is conducted in the medium of methyl ester of bromoacetic acid.

What is claimed is:

1. A process for preparing diphenylphosphinylacetic acid hydrazide comprising reacting diphenylchlorophosphine with ethylene oxide in a medium of an inert organic solvent, heating the reaction mixture in the presence of an alkyl ester of a haloacetic acid to the formation of an alkyl ester of diphenylphosphinylacetic acid, and reacting the alkyl ester of diphenylphosphinylacetic acid with hydrazine hydrate.

2. A process as claimed in claim 1, wherein said reaction of diphenylchlorophosphine with ethylene oxide is conducted at the stoichiometric ratio between the components.

3. A process as claimed in claim 1, wherein as the organic solvent use is made of an alkyl ester of a haloacetic acid.

4. A process as claimed in claim 1, wherein as the organic solvent methylene chloride is used.

5. A process as claimed in claim 1, wherein said reaction of diphenylchlorophosphine with ethylene oxide is conducted at a temperature within the range of from −5° to 20° C.

6. A process as claimed in claim 1, wherein heating of the reaction mixture is conducted at a temperature of from 60° to 140° C.

7. A process as claimed in claim 1, wherein said reaction of said alkyl ester of diphenylphosphinylacetic acid with hydrazine hydrate is conducted at a temperature within the range of from 40° to 60° C.

* * * * *